United States Patent [19]

Kikumoto et al.

[11] 4,061,776

[45] Dec. 6, 1977

[54] PHARMACEUTICALLY ACTIVE 2-OMEGA-AMINOALKOXYDIPHENYL ETHERS

[75] Inventors: Ryoji Kikumoto, Machida; Akihiro Tobe, Kawasaki; Hidenobu Ikoma, Tokyo, all of Japan

[73] Assignee: Mitsubishi Chemical Industries Ltd., Tokyo, Japan

[21] Appl. No.: 742,877

[22] Filed: Nov. 18, 1976

Related U.S. Application Data

[63] Continuation-in-part of Ser. No. 612,005, Sept. 10, 1975, abandoned.

[51] Int. Cl.² .................... A01N 9/20; A01N 9/24; C07C 93/06

[52] U.S. Cl. .................... 424/330; 260/501.18; 260/501.19; 260/570.7; 424/316; 424/248.58; 544/106

[58] Field of Search ............ 260/570.7 R, 501.18, 260/501.19; 424/316, 330

[56] References Cited

PUBLICATIONS

Toyoshima, et al., (I), "Journal Pharm. Soc. Japan," vol. 89, pp. 1078–1084, (1969).
Toyoshima, et al., (II), "Journal Pharm. Soc. Japan," vol. 89, pp. 1417–1425, (1970).

*Primary Examiner*—Robert V. Hines
*Attorney, Agent, or Firm*—Oblon, Fisher, Spivak, McClelland & Maier

[57] ABSTRACT

This invention relates to 2-omega-aminoalkoxydiphenylethers and derivatives thereof which are pharmocologically active as antidepressants.

7 Claims, No Drawings

4,061,776

PHARMACEUTICALLY ACTIVE 2-OMEGA-AMINOALKOXYDIPHENYL ETHERS

CROSS REFERENCE TO RELATED APPLICATIONS

This application is a continuation-in-part of application Ser. No. 612,005, filed Sept. 10, 1975 and now abandoned.

SUMMARY OF THE INVENTION

This invention relates to compounds of the formula (I):

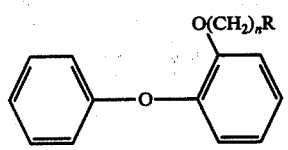

wherein R is selected from the group consisting of amino, $C_1$–$C_5$ alkylamino, and $C_2$–$C_6$ dialkylamino; $n$ is an integer of 4 or 5; and the pharmaceutically acceptable acid addition salts of said compound.

This invention also relates to a method for palliating conditions of depression in warm-blooded animals which comprises administering to said animal an antidepressant effective amount of a compound of Formula I, and a method for producing said compound which comprises reacting an omega-halogenoalkoxydiphenyl ether of the formula (II):

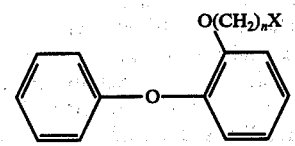

wherein X is halogen; and $n$ is as defined above, with an amine of the formula (III):

R—H    (III)

wherein R is as defined above.

DESCRIPTION OF THE INVENTION

As summarized above, this invention relates to a group of compounds useful as pharmaceutical agents, which compounds are represented by Formula I above.

Illustrative of the compounds of this invention are the following:

2-(4-aminobutoxy)diphenyl ether
2-(4-methylaminobutoxy)diphenyl ether
2-(4-dimethylaminobutoxy)diphenyl ether
2-(5-methylaminopentyloxy)diphenyl ether
2-(5-dimethylaminopentyloxy)diphenyl ether The pharmaceutically acceptable acid addition salts of the above compound are, of course, also included within the scope of this invention.

It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, succinates, adipates, propionates, tartrates, maleates, citrates, benzoates, toluenesulfonates, and methanesulfonates.

Of the compounds of this invention, it will be understood that the following compounds are most preferred due to their high level of anti-depressant activity and their low level of toxicity.

2-(4-methylaminobutoxy)diphenyl ether
2-(4-dimethylaminobutoxy)diphenyl ether
2-(5-methylaminopentyloxy)diphenyl ether

PREPARATION

The compounds of this invention are prepared by reacting an omega-halogenoalkoxydiphenyl ether with an amine.

The omega-helogenoalkoxydiphenyl ether starting materials which are represented by Formula II above can be prepared by reacting 2-hydroxydiphenyl ether with 1,4-dihalogenobutane or 1,4-dihalogenopentane in the presence of an alkali.

The amine starting materials which are represented by Formula III above include ammonia; primary amines such as methylamine, ethylamine, isopropylamine and the like; and secondary amines such as dimethylamine, diethylamine, N-methylethylamine and the like.

The amine reacts with the equimolecular amount of the omega-halogenoalkoxydiphenylether. However, the use of the excess amine accelerates the reaction. Normally, the amount of the amine to be employed is in the range of 1 to 100 moles per 1 mole of the omega-halogenoalkoxydiphenyl ether.

The reaction can be carried out without an added solvent. However, the use of a reaction-inert solvent makes a homogenous reaction possible.

Examples of such solvents are water, dioxane, tetrahydrofuran, dimethyl sulfoxide, lower aliphatic alcohols and the mixtures thereof. The reaction temperature is not critical, but normally ranges from room temperature to 150° C. The reaction time varies widely with the reaction temperature and the reactivity of the starting materials, but normally is in the range of from 10 minutes to 40 hours.

The presence of bases which neutralize a hydrogen halide formed in the course of the reaction accelerates the reaction.

Examples of such bases are inorganic bases such as potassium hyroxide, sodium hydroxide, potassium carbonate, sodium carbonate and the like; and tertiary amines such as pyridine, triethylamine and the like.

The amount of the base to be employed is normally in the range of 1 to 5 moles per 1 mole of the omega-halogenoalkoxydiphenyl ether.

When the base is absent, the omega-aminoalkoxydiphenyl ether reacts with a hydrogen halide formed during the reaction, and is converted to the acid addition salts thereof.

Acid addition salts of the 2-omega-aminoalkoxydiphenyl ethers may be conveniently prepared by contacting the compounds with a suitable acid.

The 2-omega-aminoalkoxydiphenyl ethers and the acid addition salts thereof may be purified by recrystallization employing a suitable solvent such as alcohol-ether.

Pharmacological testing of the 2-omega-aminoalkoxydiphenyl ethers has demonstrated that they are useful as antidepressant agents as evidenced by their ability to reverse reserpine hypothermia in mice.

Anticonvulsant activity has also been found in the compounds of this invention.

The compounds have been tested in mice for antidepressant, sedative, anticonvulsant and anticholinergic activity. The compounds were administered intraperitoneally and activities of the compounds were compared with those of Amitriptyline.

Antidepressant activity was evaluated by antgonism of reserpine (5 mg/kg i.p.) induced hypothermia (P.S.J. Spencer in "Antidepressant Drugs" S. Garattini and M. N. G. Duhes, ed, Excerpta Medica Foundation, Amsterdam, pages 194–204 (1967) and antireserpine activity was expressed as relative potency (Amitriptyline = 1).

LD50 was calculated by Litchfield-Wilcoxon method.

CNS depressant activity was defined by the ability of the compounds to cause neurological deficit as measured by traction test (S. Courvoisier, R. Ducrot, L. Julou; "Psychotropic Drugs" ed. by S. Garattini, V. Ghetti, page 373, (1957)) and spontaneous motor activity (Spontaneous motor activity was measured by ANIMEX apparatus).

Anticonvulsant activity was determined by antagonism of electroshock induced tonic extensor (L. S. Goodman, M. Singh Grewal, W. C. Brown and E. A. Swinyard, J. Pharmacol, Exptal. Therap., 108, 168 (1953) ).

Central anticholinergic effect was assessed by testing the tremorine induced tremor in mice (G. M. Everett, L. E. Bloucus and J. M. Sheppard, Science 124 79 (1956) ).

Results are summarized in Table 1, which show compounds within as well as outside the scope of the present invention, in which ED50 is defined as the dose of the test compounds, which prevent 50% of each response.

TABLE I

| Antireserpine Activity in Mice | | |
|---|---|---|
| Compound | Relative Potency | LD50 mg/kg i.p. |
| 2-(2-dimethylaminoethoxy)diphenyl ether chloride | 0 | — |
| 2-(3-dimethylaminopropoxy)diphenyl ether hydrochloride | 0.14 | — |
| 2-(3-methylaminopropoxy)diphenyl ether hydrochloride | 0.28 | — |
| 2-(4-aminobutoxy)diphenyl ether hydrochloride | 0.28 | — |
| 2-(4-methylaminobutoxy)diphenyl ether hydrochloride | 1.10 | 100 |
| 2-(4-dimethylaminobutoxy)diphenyl ether hydrochloride | 0.58 | 92 |
| 2-(5-methylaminopentyloxy)diphenyl ether hydrochloride | 0.57 | 85 |
| 2-(5-dimethylaminopentyloxy)diphenyl ether hydrochloride | 0.24 | — |
| 2-(4-morpholinobutoxy)diphenyl ether hydrochloride | 0.21 | — |
| Amitriptyline | 1.00 | 65 |

The results in Table I show that the compounds within the scope of the present invention are generally superior with respect to antidepressant activity than other diphenylether hydrochloride compounds outside the scope of the present invention. Of course, the preferred 4-methylaminobutoxy-, 4-dimethylaminobutoxy- and 5-methylaminopentyloxy diphenylether hydrochloride compounds exhibit the best activity of all compounds of the present invention tested.

TABLE II

| | CNS Depressant, Anticonvulsant and Central Anticholinergic Activity in Mice | | | |
|---|---|---|---|---|
| Compound | Anti-Convulsant Activity ED50 (mg/kg i.p.) | Muscle Relaxant Action ED50 (mg/kg i.p.) | Spontaneous Motor Activity Depression ED50 (mg/kg i.p.) | Antitremorine Effect ED50 (mg/kg i.p.) |
| 2-(4-methyl-aminobutoxy)-diphenyl ether hydrochloride | 32 | 60 | 60 | 30 |
| Amitriptyline | 16 | 15 | 18 | 4 |

It will be apparent from Tables I and II that 2-(4-methylaminobutoxy) diphenyl ether exhibits antireserpine activity comparable to that of Amitriptyline, while it exhibits low toxicity, weak CNS depressant and anticholinergic action. The compounds of this invention can be administered by any means that effects palliating conditions of depression in warm-blooded animals. For example, administration can be parenterally, subcutaneously, intravenously, intramuscularly, or intraperitoneally. Alternatively or concurrently, administration can be by the oral route. The dosage administered will be dependent upon the age, health and weight of the recipient, the extent of depression, kind of concurrent treatment if any, frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result.

The compound of Formula I can be employed in dosage forms such as tablets, capsules, powder packets, or liquid solutions, suspension, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

Besides the active ingredient of this invention, the composition will contain a solid or liquid non-toxic pharmaceutical carrier for the active ingredient. In one embodiment of a composition, the solid carrier can be a capsule of the ordinary gelatin type. In the capsule will be from about 30–60% by weight of a compound of Formula I and 70–40% of a carrier. In another embodiment, the active ingredient can be tableted with or without adjuvants, or put into powder packets. These capsules, tablets and powders will generally constitute from about 5% to about 95% and preferably from 25% to 90% by weight of active ingredient. These dosage forms preferably contain from about 5 to 500 mg of active ingredients, with from about 25 to 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as ethylene glycol, propylene glycol and polyethylene glycol are preferred liquid carriers, particularly for injectible solutions such as saline will ordinarily contain from about 0.5% to 20% and preferably about 1 to 10% by weight of the active ingredient.

As mentioned above, oral administration can be in a suitable suspension or syrup, in which the active ingredient normally will constitute from about 0.5 to 10% by weight. The pharmaceutical carrier in such composition can be a watery vehicle such as an aromatic water, a syrup or a pharmaceutical mucilage.

The following examples are presented to further illustrate the preparation of the compounds of this invention.

EXAMPLE 1

A solution of 5.0 g of 2-(4-bromobutoxy)diphenyl ether 30 ml of 40% dimethylamine aqueous solution, and 100 ml of ethanol is allowed to stand at room temperature for 8 hours. Ethanol and excess dimethylamine are distilled in vacuo, 2N-NaOH aqueous solution is added, and the reaction product is extracted with ether. The ether solution is distilled, 2N-HCl solution is added and the solution is evaporated to dryness.

The residue is recrystallized from ethanol-ether to give 4.6 g (89% yield) of 2-(4-dimethylaminobutoxy)-diphenyl ether hydrochloride, m.p. 131°–135° C.

Analysis-Calc'd. for $C_{18}H_{23}NO_2 \cdot HCl$ (percent): C, 67.17; H, 7.52; N, 4.35; Found (percent): C, 67.35; H, 7.46: N, 4.25.

EXAMPLE 2

A solution of 5.0 g of 2-(5-bromopentyloxy)diphenyl ether and 6 g of methylamine in 100 ml of ethanol is heated at a temperature of 50° C for 2 hours in a sealed tube. Ethanol and excess methylamine are distilled in vacuo, 2N-NaOH aqueous solution is added, and the reaction product is extracted with ether. Dry hydrogen chloride gas is passed into the ether solution, and the precipitate collected by filtration period, Recrystalliza-tion from ethanol-ether gives 4.2 g (88% yield) of 2-(5-methylaminopentyloxy)diphenyl ether hydrochloride, m.p. 88°–90° C.

Analysis Calc'd. for $C_{18}H_{23}NO_2 \cdot HCl$ (percent): C, 67.17; H, 7.52; N, 4.35; Found (percent): C, 67.30; H, 7.64; N, 4.37.

EXAMPLES 3–5

The compounds in the following table were prepared according to the procedure described in Example 1 or 2, using the appropriate starting materials.

| Example Number | Compound Formula | Addition Moiety | Preparation Process (Ex. No.) | m.p. (° C) | Analysis Upper: Calcd. Lower: Found | | |
|---|---|---|---|---|---|---|---|
| | | | | | C | H | N |
| 3 | [2-phenoxyphenyl]-O-(CH$_2$)$_4$NHCH$_3$ | HCl | 2 | 112–116 | 66.33 / 66.60 | 7.20 / 7.18 | 4.55 / 4.47 |
| 4 | [2-phenoxyphenyl]-O-(CH$_2$)$_5$N(CH$_3$)$_2$ | HCl | 1 | 104–108 | 67.94 / 67.85 | 7.80 / 7.93 | 4.17 / 4.16 |
| 5 | [2-phenoxyphenyl]-O-(CH$_2$)$_4$NH$_2$ | HCl | 1 | 93–95 | 65.41 / 65.70 | 6.86 / 6.96 | 4.77 / 4.66 |

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A compound having the formula (I):

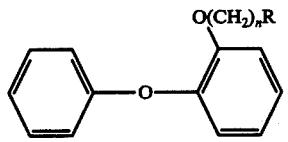

wherein R is selected from the group consisting of amino, $C_1$–$C_5$ alkylamino, and $C_2$–$C_6$ dialkylamino; n is an integer of 4 or 5; or a pharmaceutically acceptable acid addition salt thereof.

2. The compound of claim 1, wherein R is selected from the group consisting of amino, methylamino, and dimethylamino.

3. The compound of claim 1, which is 2-(4-methylaminobutoxy)diphenyl ether.

4. The compound of claim 1, which is 2-(4-dimethylaminobutoxy)diphenyl ether.

5. The compound of claim 1, which is 2-(5-methylaminopentyloxy)diphenyl ether.

6. A method for palliating conditions of depression in warm-blooded animals, which comprises:
administering to said animal an antidepressant effective amount of a compound of the formula (I):

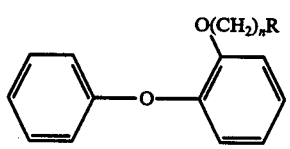
(I)
wherein R is selected from the group consisting of amino, $C_1$-$C_5$ alkylamino, and $C_2$-$C_6$ dialkylamino; and n is an integer of 4 or 5; or a pharmaceutically acceptable acid addition salt thereof.
7. An antidepressant composition which comprises an antidepressant effective amount of a compound of claim 1 and a pharmaceutically acceptable carrier.
* * * * *

UNITED STATES PATENT AND TRADEMARK OFFICE
CERTIFICATE OF CORRECTION

PATENT NO. : 4,061,776
DATED : December 6, 1977
INVENTOR(S) : Kikumoto et al

It is certified that error appears in the above-identified patent and that said Letters Patent are hereby corrected as shown below:

Under the heading "[75] Inventors:" before "Hidenobu Ikoma, Tokyo" insert --Shinji Tonomura, Tokyo--.

Signed and Sealed this

Second Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO.  : 4,061,776
DATED       : December 6, 1977
INVENTOR(S) : RYOJI KIKUMOTO ET AL It is certified that error appears in the above-identified patent and that said Letters Patent are hereby corrected as shown below:

Column 2, line 19, delete "1,4-dihalogenopentane" and insert --1,5-dihalogenopentane--.

Column 3, line 44, delete "124" and insert --$\underline{124}$--.

Column 5, line 46, after "ether" insert --,--.

Column 5, line 56, delete "No$_2$" and insert --NO$_2$--.

Column 5, line 68, delete "period".

Column 6, Claim 1, to the right of the formula insert --(I)--.

Signed and Sealed this

Thirteenth Day of June 1978

[SEAL]

Attest:

RUTH C. MASON
Attesting Officer

DONALD W. BANNER
Commissioner of Patents and Trademarks